United States Patent [19]
Jarvik et al.

[11] Patent Number: 5,851,174
[45] Date of Patent: Dec. 22, 1998

[54] CARDIAC SUPPORT DEVICE

[75] Inventors: Robert Jarvik, 124 W. 60 St., New York, N.Y. 10023; Daniel E. Alesi, Sherman, Conn.

[73] Assignees: Robert Jarvik, New York, N.Y.; United States Surgical Corporation, Norwalk, Conn.

[21] Appl. No.: 714,898

[22] Filed: Sep. 17, 1996

[51] Int. Cl.$^6$ ............................................. A61M 1/10
[52] U.S. Cl. ............................................. 600/16; 415/900
[58] Field of Search ................. 623/3; 600/16–18; 415/900

[56] References Cited

U.S. PATENT DOCUMENTS

| | | |
|---|---|---|
| Re. 28,742 | 3/1976 | Rafferty et al. . |
| 2,635,547 | 4/1953 | Cataldo . |
| 3,608,088 | 4/1969 | Dorman et al. . |
| 3,647,324 | 3/1972 | Rafferty et al. . |
| 3,685,059 | 8/1972 | Bokros et al. . |
| 3,957,389 | 5/1976 | Rafferty et al. . |
| 3,995,617 | 12/1976 | Watkins et al. . |
| 4,037,984 | 7/1977 | Rafferty et al. . |
| 4,135,253 | 1/1979 | Reich et al. . |
| 4,382,199 | 5/1983 | Isaacson . |
| 4,507,048 | 3/1985 | Belenger et al. . |
| 4,589,822 | 5/1986 | Clausen et al. . |
| 4,625,712 | 12/1986 | Wampler . |
| 4,688,998 | 8/1987 | Olsen et al. . |
| 4,704,121 | 11/1987 | Moise . |
| 4,753,221 | 6/1988 | Kensey et al. ............... 600/16 |
| 4,763,032 | 8/1988 | Bramm et al. . |
| 4,779,614 | 10/1988 | Moise ............................ 623/3 |
| 4,817,586 | 4/1989 | Wampler . |
| 4,846,152 | 7/1989 | Wampler et al. . |
| 4,895,493 | 1/1990 | Kletschka . |
| 4,906,229 | 3/1990 | Wampler . |
| 4,908,012 | 3/1990 | Moise et al. . |
| 4,927,407 | 5/1990 | Dorman . |
| 4,944,722 | 7/1990 | Carriker et al. . |
| 4,957,504 | 9/1990 | Chardack . |

(List continued on next page.)

FOREIGN PATENT DOCUMENTS

| | | |
|---|---|---|
| 1503906 | 10/1966 | France . |
| 1514319 | 1/1967 | France . |

OTHER PUBLICATIONS

"An Artificial Heart That Doesn't Beat?", Journal of American Medical Association, Feb. 18, 1974, vol. 227, No. 7, pp. 735, 738.

Primary Examiner—William E. Kamm
Assistant Examiner—George R. Evanisko

[57] ABSTRACT

An apparatus for pumping blood includes an elongated housing dimensioned to be at least partially positioned within the heart of a patient, a rotating member supported for rotational movement within the elongated housing and a drive mechanism for imparting rotational movement to the rotating member. The elongated housing includes an outer wall, a first inlet port for permitting blood to enter the elongated housing through a first end of the elongated housing and a second inlet port defined in the outer wall of the elongated housing for permitting blood to enter through the outer wall. The rotating member is rotatable to impart pumping energy to the blood entering through the first and second inlet ports to direct the blood through an outlet opening of the elongated housing. The rotating member preferably includes first and second blood pumping blade arrangements. The first blade arrangement is dimensioned to impart pump energy to the blood entering the elongated housing through the first inlet port. The second blade arrangement is dimensioned to at least impart pump energy to the blood entering the elongated housing through the second inlet port. The electric motor stator and rotor define a space therebetween through which blood entering the first inlet passes. The motor is an ironless core copper electromagnetic windings which provides a sufficiently large air space for blood flow.

24 Claims, 10 Drawing Sheets

U.S. PATENT DOCUMENTS

| | | | |
|---|---|---|---|
| 4,964,864 | 10/1990 | Summers et al. | 623/3 |
| 4,969,865 | 11/1990 | Hwang et al. . | |
| 4,984,972 | 1/1991 | Clausen et al. . | |
| 4,994,078 | 2/1991 | Jarvik . | |
| 4,995,857 | 2/1991 | Arnold . | |
| 5,049,134 | 9/1991 | Golding et al. . | |
| 5,055,005 | 10/1991 | Kletschka . | |
| 5,092,879 | 3/1992 | Jarvik . | |
| 5,112,292 | 5/1992 | Hwang et al. . | |
| 5,112,349 | 5/1992 | Summers et al. . | |
| 5,118,264 | 6/1992 | Smith . | |
| 5,145,333 | 9/1992 | Smith . | |
| 5,147,388 | 9/1992 | Yamazaki . | |
| 5,344,443 | 9/1994 | Palma et al. . | |
| 5,376,114 | 12/1994 | Jarvik | 600/16 |
| 5,385,581 | 1/1995 | Bramm et al. . | |
| 5,437,601 | 8/1995 | Runge . | |
| 5,441,535 | 8/1995 | Takahashi et al. . | |
| 5,442,503 | 8/1995 | Yamane | 600/16 |
| 5,443,503 | 8/1995 | Yamane . | |
| 5,456,715 | 10/1995 | Liotta . | |
| 5,470,208 | 11/1995 | Kletschka . | |
| 5,507,629 | 4/1996 | Jarvik . | |
| 5,527,159 | 6/1996 | Bozemn, Jr. et al. | 415/900 |

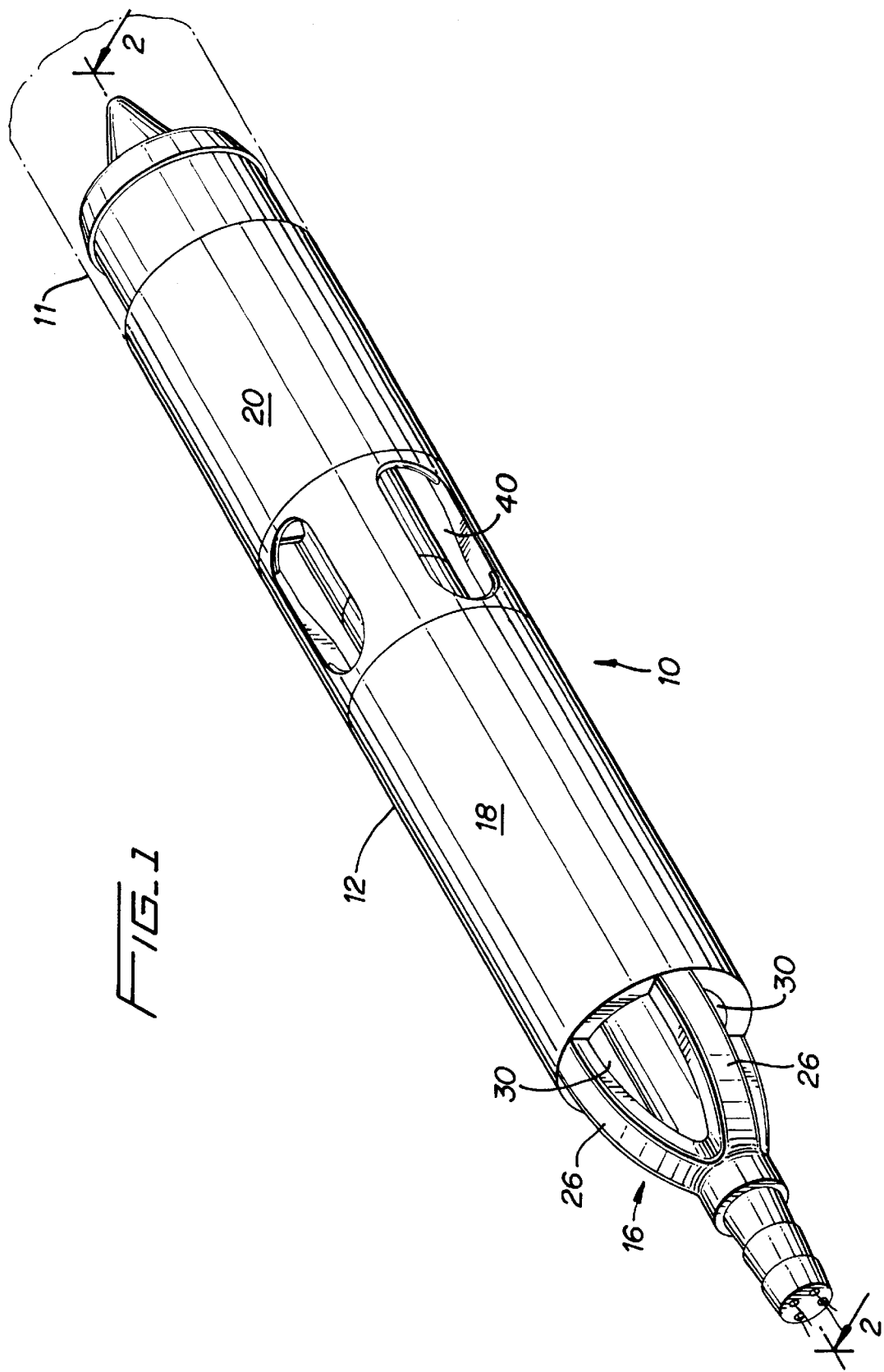

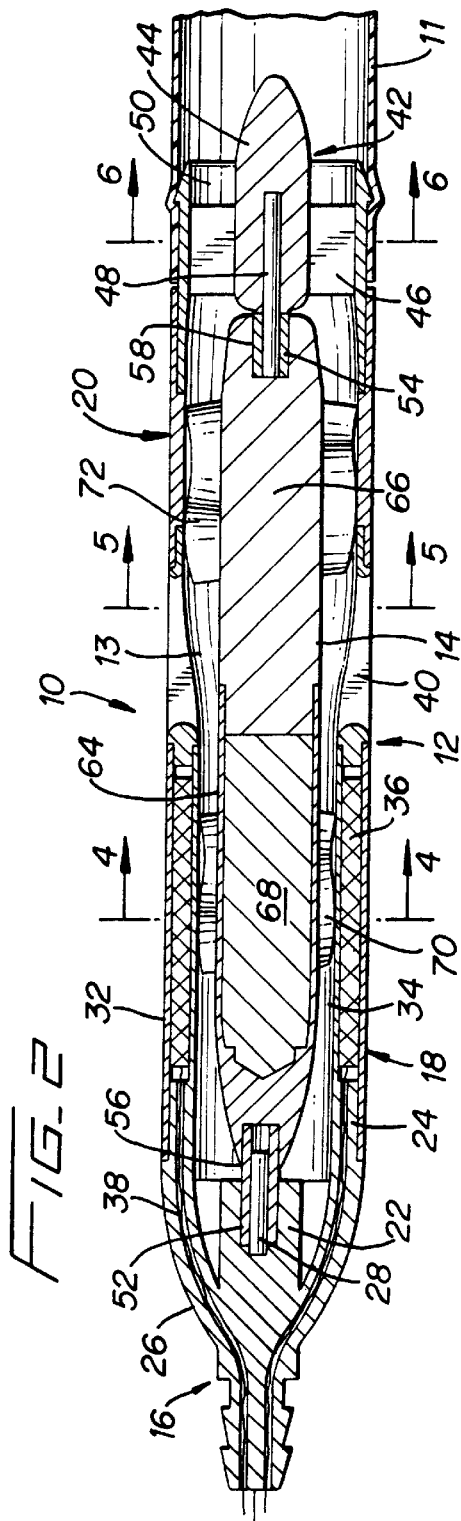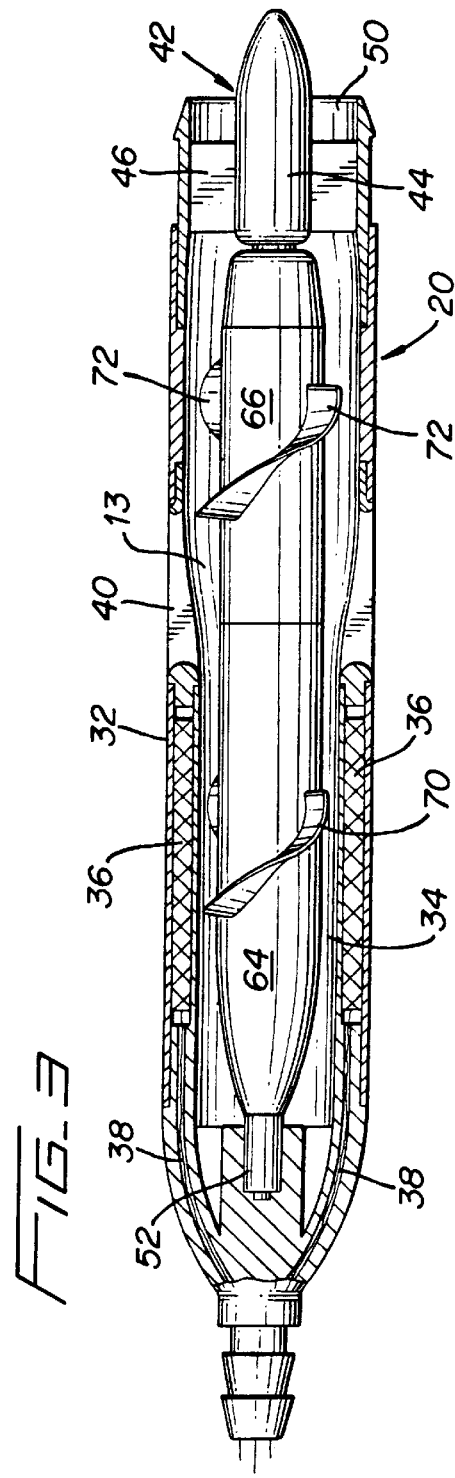

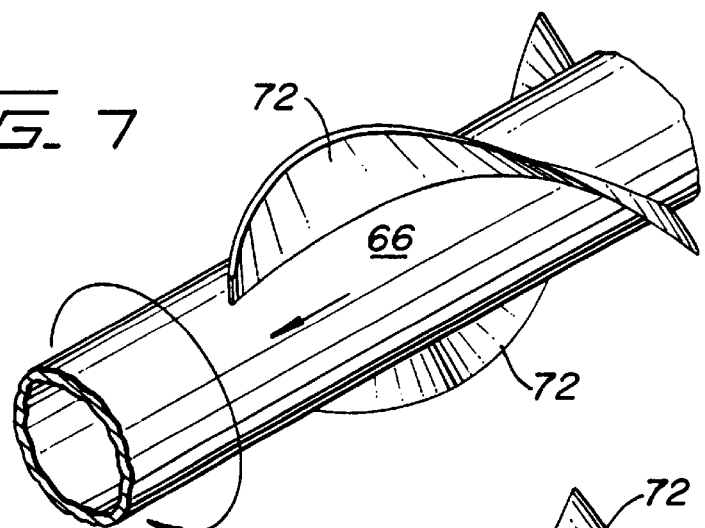
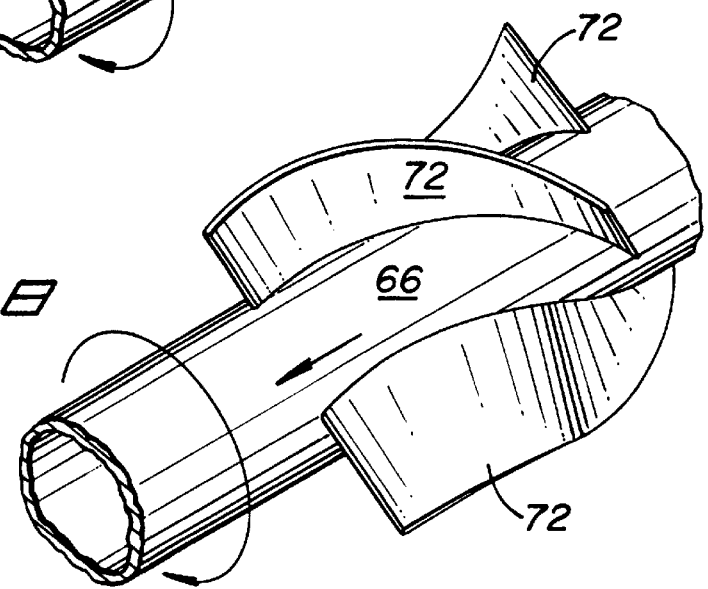
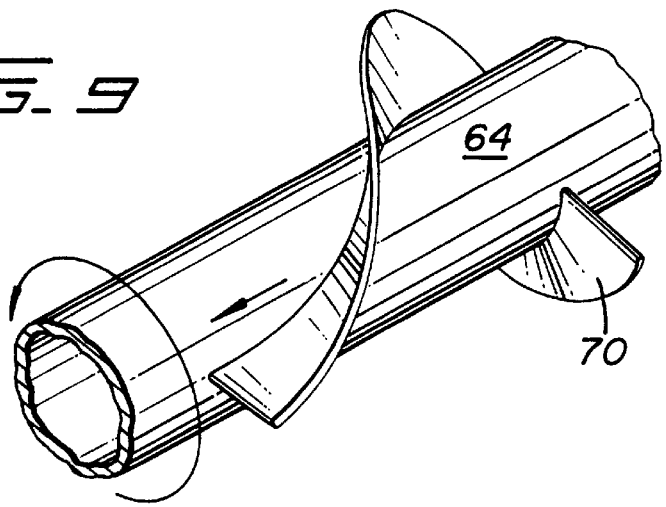

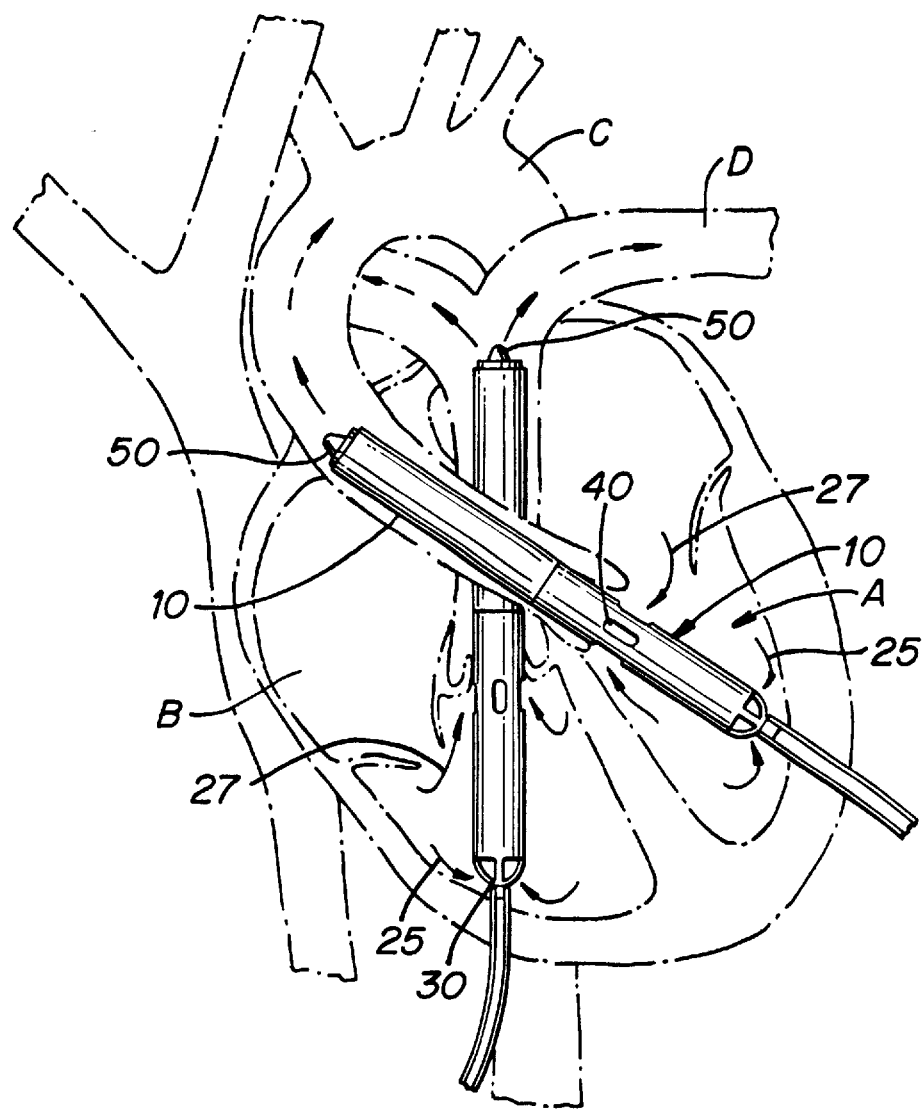
FIG_11

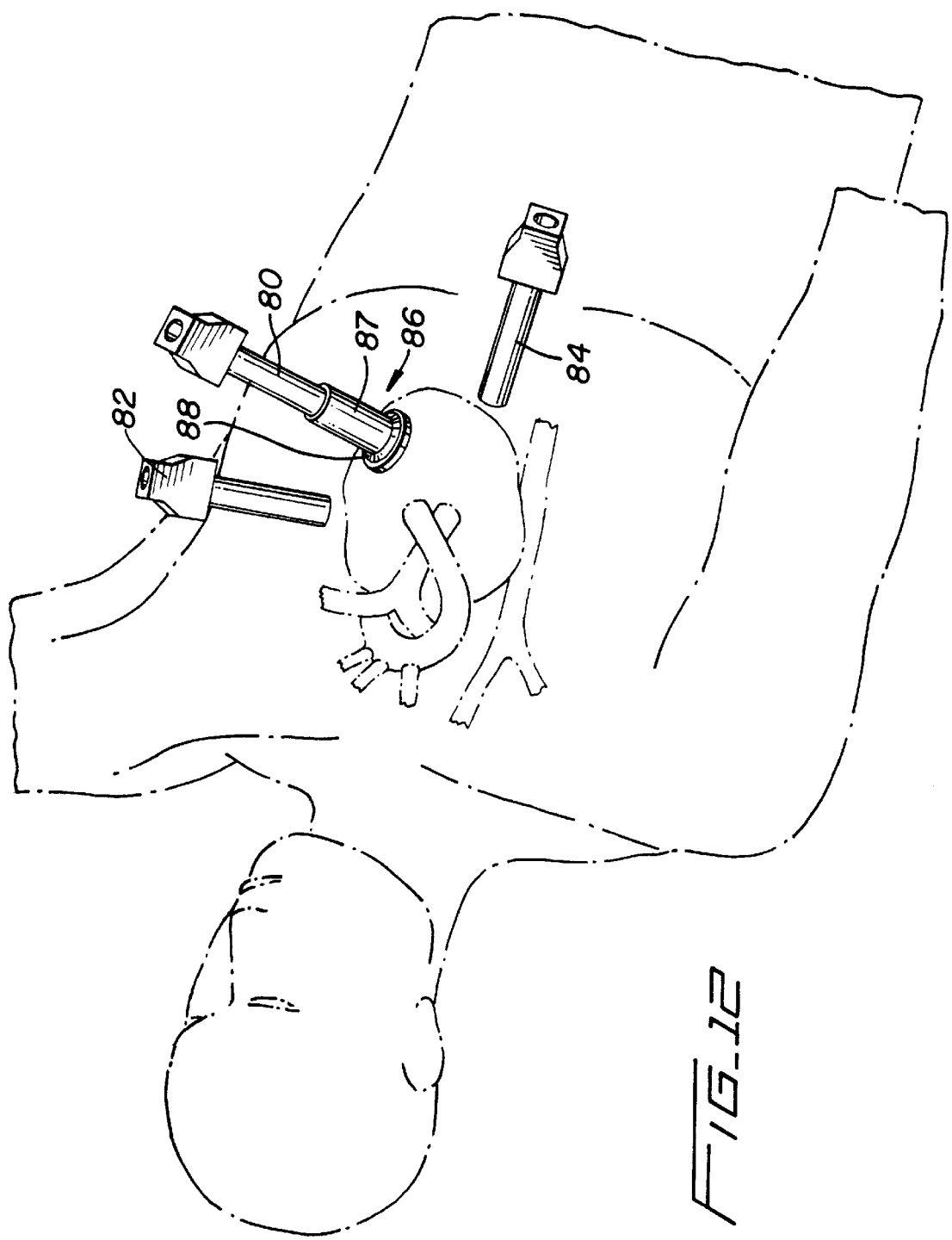

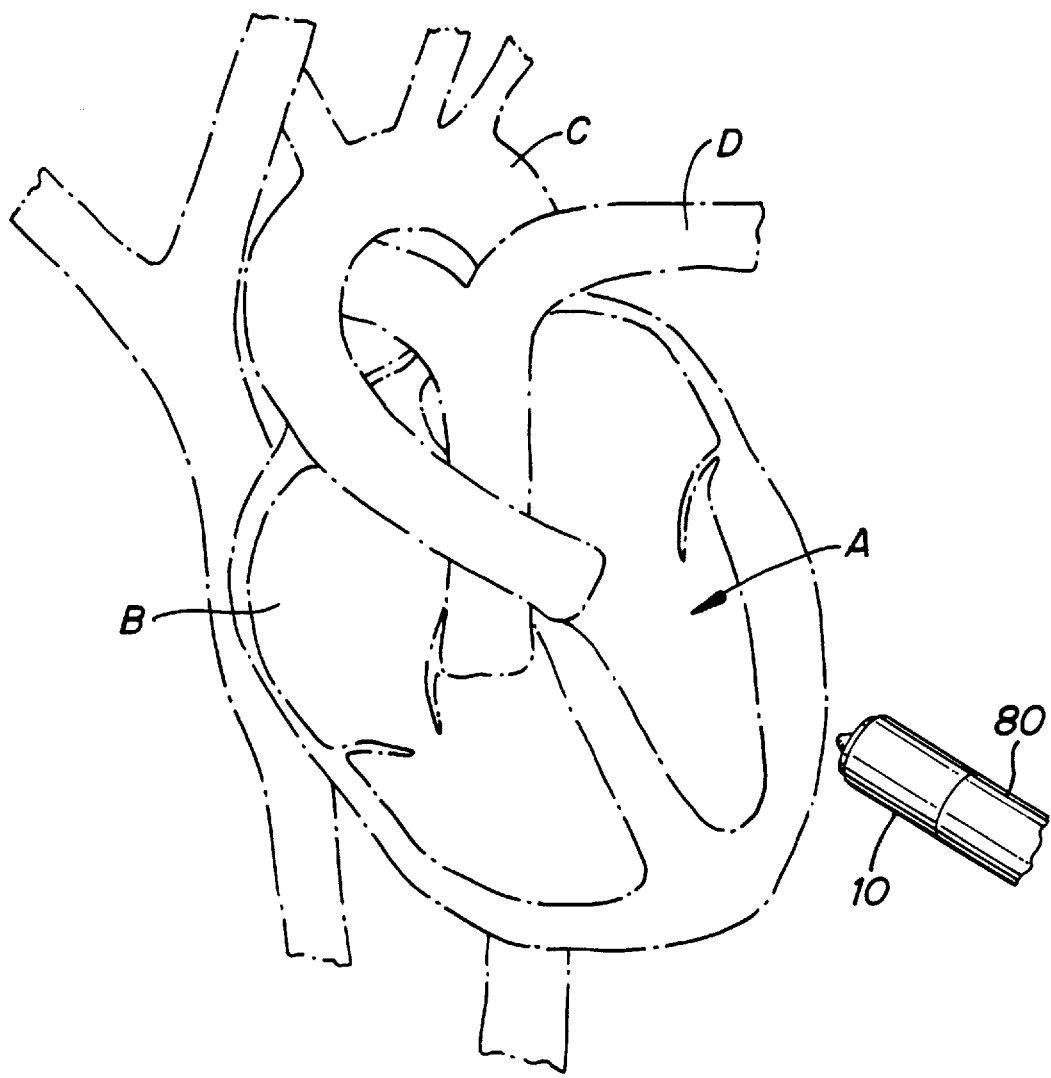
FIG_13

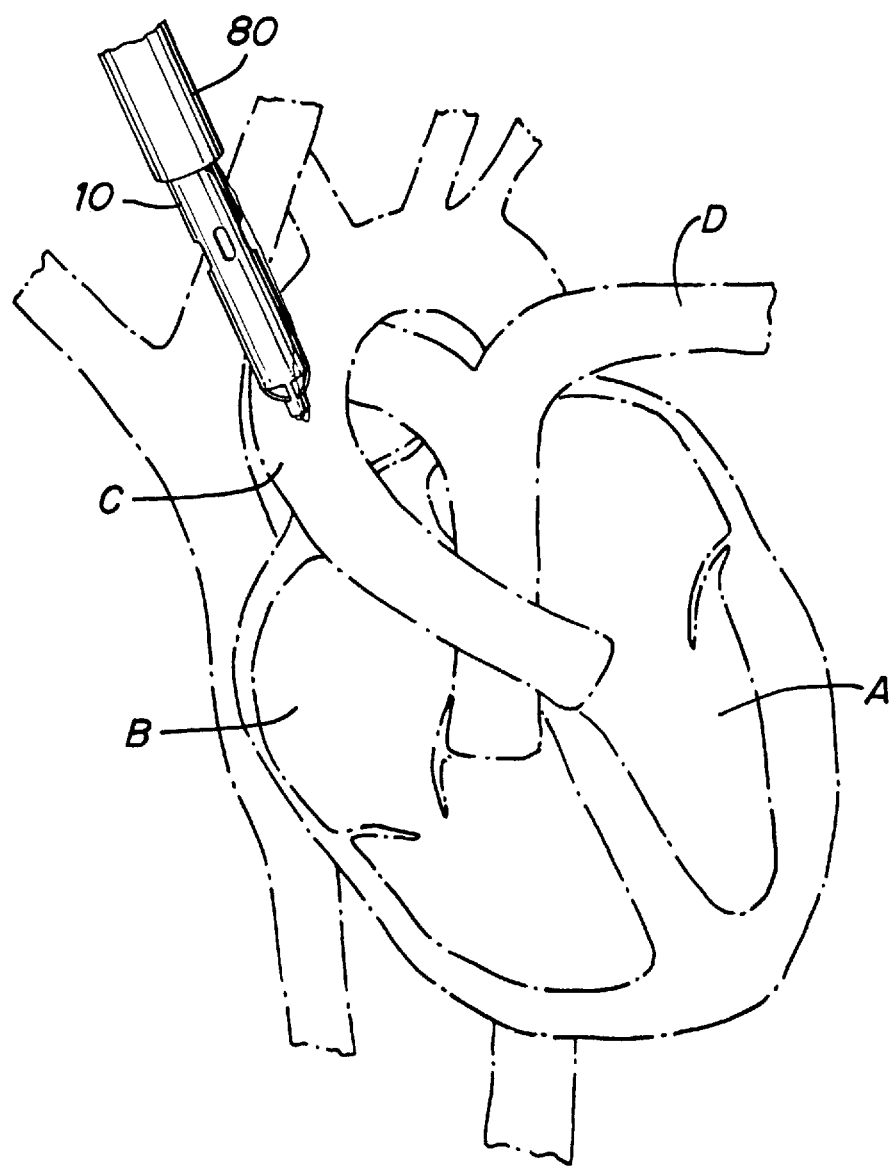
FIG_14

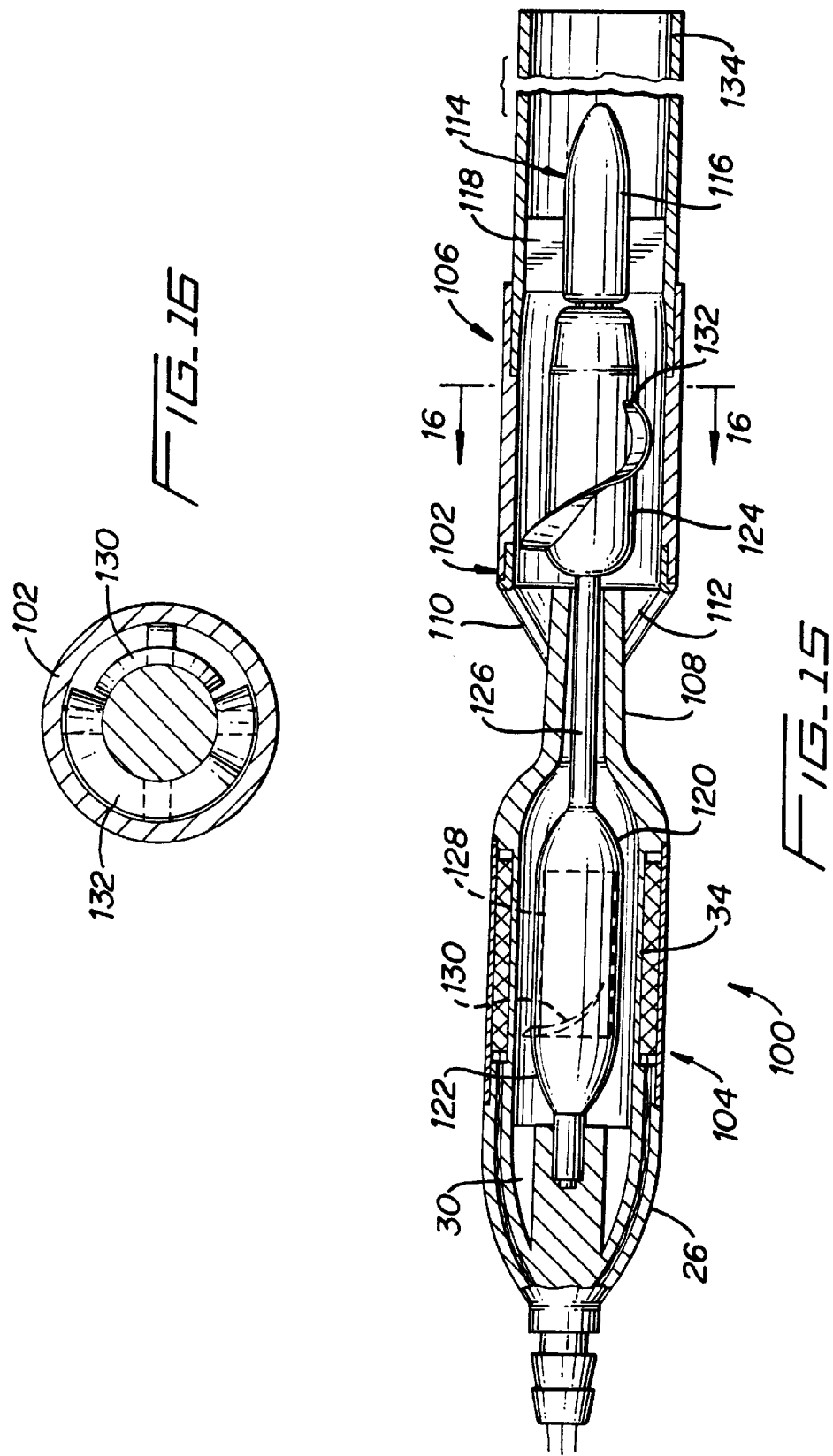

CARDIAC SUPPORT DEVICE

BACKGROUND

1. Field of the Disclosure

The present disclosure relates generally to cardiac support devices, and, more particularly, to a cannula pump which is implantable in the heart.

2. Description of the Relevant Art

Mechanical blood pumps are commonly utilized to temporarily support or substitute the pumping function of the heart during heart surgery or during periods of heart failure. The most widely applied blood pumps include roller pumps and centrifugal pumps. Typically, these pumps are a component of a cardiopulmonary bypass system (e.g., a heart-lung machine) which includes an oxygenator, a heat exchanger, blood reservoirs and filters, and tubing which transports the blood from the patient through the bypass system and back to the patient. With these systems, blood is withdrawn from the patient via an uptake cannula positioned within the vena cavae and atria or ventricles of the heart, transported through the bypass system located outside the patient's body, and pumped back into the pulmonary artery and aorta via a return cannula.

Although these cardiopulmonary bypass systems have been generally effective, they are subject to certain disadvantages. In particular, these bypass systems are relatively complicated and expensive to manufacture, expose the blood to a high surface area of foreign materials which ultimately damages the blood, require full anticoagulation, and require considerable set up time and continual management by a skilled technician (perfusionist), which also adds to the expense of the procedure.

PCT WO 94/09835 to Robert Jarvik discloses a cannula pump for temporary cardiac support. The Jarvik cannula pump includes an elongated cannula housing having a miniature rotary pump disposed therein and an electric motor which drives the rotary pump via a small shaft. The rotary pump is mounted for rotational movement about blood-immersed mechanical bearings. The cannula pump is inserted into one of the ventricles of the heart through a small incision. In one embodiment, the electric motor is miniaturized to be positioned within the heart.

Although the Jarvik cannula pump has shown great potential as a device to supplement or replace the total pumping function of the heart during, e.g., bypass surgery, the present disclosure is directed to further improvements of the Jarvik cannula pump whereby the pumping capacity is improved by, for example, the provision of two pumping sections and where concerns regarding sealing between the stationary and moving parts are essentially eliminated by directing the blood flow through the sealed electric motor.

SUMMARY

The present disclosure relates to an apparatus for pumping blood comprising an elongated housing dimensioned to be at least partially positioned within the heart of a patient, a rotating member supported for rotational movement within the elongated housing and a drive mechanism for imparting rotational movement to the rotating member. The elongated housing includes an outer wall, at least a first inlet port for permitting blood to enter the elongated housing through a first end of the elongated housing and at least a second inlet port defined in the outer wall of the elongated housing for permitting blood to enter through the outer wall. The rotating member is rotatable to impart pumping energy to the blood entering through the first and second inlet ports to direct the blood through an outlet opening of the elongated housing.

The rotating member preferably includes first and second blood pumping blade arrangements (although one blade arrangement is also contemplated). The first blade arrangement is dimensioned to impart pump energy to the blood entering the elongated housing through the first inlet port. The second blade arrangement is dimensioned to impart pump energy to the blood entering the elongated housing through the second inlet port as well as the first inlet port.

The drive mechanism of the apparatus may be enclosed within the elongated housing. The drive mechanism preferably includes an electric motor incorporating a magnetically actuated rotor and a motor stator where the rotor is embedded within the rotatable member. The motor stator and the rotatable member define an annular space therebetween through which blood entering the first inlet passes and is acted upon by the first blade arrangement.

A method for supporting all or part of the pumping function of a heart by endoscopically inserting the apparatus is also disclosed.

BRIEF DESCRIPTION OF THE DRAWINGS

Preferred embodiments of the disclosure are described hereinbelow with reference to the drawings wherein:

FIG. 1 is a perspective view of the cardiac support device in accordance with the principles of the present disclosure;

FIG. 2 is a cross-sectional view of the cardiac support device taken along lines 2—2 of FIG. 1;

FIG. 3 is a side plan view of the cardiac support device in partial cross-section illustrating one embodiment of the configuration of the impeller blades of the rotating member (with the flexible cannula removed);

FIG. 7 is a perspective view of the impeller blade structure of the cardiac support device of FIG. 2;

FIG. 8 is a perspective view of an alternate impeller blade structure;

FIG. 9 is a perspective view of another alternate impeller blade structure;

FIG. 11 is a schematic drawing of the heart illustrating a first cardiac support device inserted through the apex of the left ventricle with the out-flow across the aortic valve into the aorta and a second cardiac support device inserted across the apex of the right ventricle with the outflow across the pulmonic valve into the pulmonary artery;

FIG. 12 is a view illustrating an alternate method for applying the cardiac support device where endoscopic techniques are incorporated, illustrating a first endoscopic portal for delivering the device and a second endoscopic portal for permitting the introduction of an endoscopic viewing apparatus;

FIG. 13 is a view illustrating the cardiac support device introduced through the endoscopic portal to be positioned within the apex of the heart;

FIG. 14 illustrates an alternate method for applying the cardiac support device utilizing endoscopic techniques where the aorta is accessed and the cardiac support device is inserted within the aorta for positioning within the heart;

FIG. 15 is a side plan view in partial cross-section of an alternate embodiment of the cardiac support device of FIG. 1; and FIG. 16 is a cross-sectional view of the cardiac support device of FIG. 15 taken along lines 16—16.

DETAILED DESCRIPTION OF THE PREFERRED EMBODIMENT(S)

Figure 4:
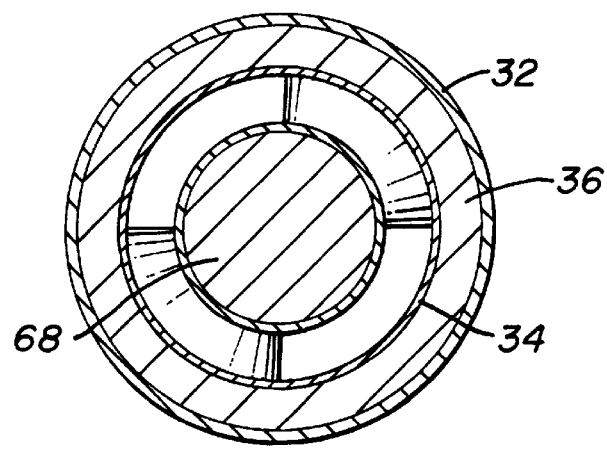
FIG. 4 is a cross-sectional view of the cardiac support device taken along lines 4—4 of FIG. 2.

Referring now in detail to the drawings wherein like reference numerals identify similar or like components throughout the several views, FIGS. 1–2 illustrate a preferred embodiment of the cardiac support device or cannula heart pump in accordance with the principles of the present disclosure. Support device 10 may be used to supplement or totally replace the pumping function of the heart during cardiac surgery, during temporary periods of heart failure and during medical emergencies involving severe heart failure. Support device 10 is advantageously dimensioned to be positioned within either the left or right ventricle of a patient's heart and preferably has a length ranging from about 2 to about 3 inches and a diameter ranging from about 9 to 12 millimeters, and is more preferably 2 inches in length with a diameter of 10 mm. Flexible cannula 11, only a portion of which is illustrated in FIG. 1, is placed over support device 10, and preferably has a length of 1–4 inches and substantially the same diameter as the device 10.

Support device 10 includes generally cylindrically-shaped cannula housing 12 having an elongated opening or axial bore 13 and a rotating member 14 coaxially mounted within the bore 13. Cannula housing 12 has three component parts or sections integrally connected to each other by conventional means to form a single cannula unit. The sections include first or inlet section 16, second or intermediate section 18 and third or exit section 20.

Inlet section 16 includes a central hub 22, and a plurality of spokes 26 (e.g., four) extending contiguously from the cylindrical portion 24 interconnecting central hub 22 and cylindrical portion 24. Central hub 22 houses stationary bearing pin 28 which supports the proximal end of rotating member 14. A plurality of axial openings 30 (FIG. 1) defined between adjacent spokes 26 form blood inlet ports to permit the axial inflow of blood into cannula housing 12 as will be discussed below.

Referring now to FIGS. 2–3, in conjunction with the axial cross-sectional view of FIG. 4, intermediate section 18 of cannula housing 12 accommodates the drive mechanism or electric motor unit of the device 10 and includes an outer tube 32 and an inner tube 34 coaxially mounted within the outer tube 32. Outer tube 32 and inner tube 34 define a generally annular space therebetween which accommodates and effectively seals the electromagnetic wire windings 36 of the motor unit. In a preferred embodiment, electromagnetic wire windings 36 are fabricated from copper and the motor is an ironless core design for reasons which will be discussed below. Electromagnetic windings 36 are in electrical contact with a plurality of electrical wires 38 which supply the electric current necessary to generate the electromagnetic fields required to rotate rotating member 14. Electrical wires 38 are embedded within spokes 26 of housing 12 and extend from the spokes 26 to an electric source located outside the body.

Figure 5:
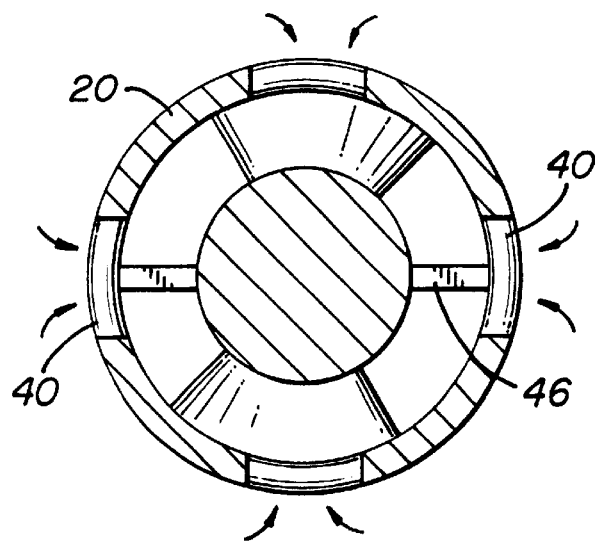
FIG. 5 is a cross-sectional view of the cardiac support device taken along lines 5—5 of FIG. 2.
Figure 6:
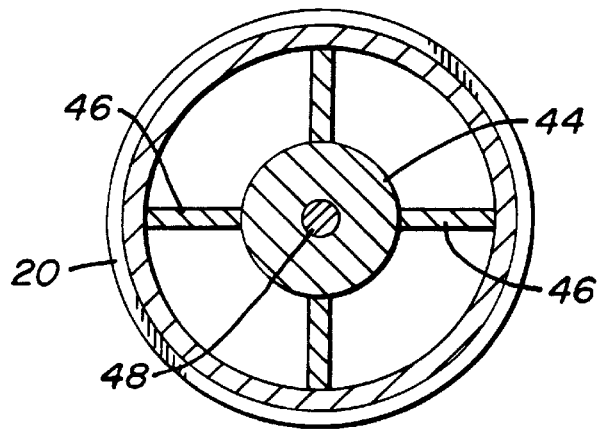
FIG. 6 is a cross-sectional view of the cardiac support device taken along lines 6—6 of FIG. 2.

Referring now to FIGS. 1–3, in conjunction with the axial cross-sectional view of FIG. 5, third section 20 of cannula housing 14 defines the pump chamber or pump housing of device 10 and has a plurality of elongated axial slots 40 formed in its outer surface at a location adjacent second section 18. Although four axial slots 40 are shown, a different number of slots as well as slots of different configurations are also contemplated. Axial slots 40 are preferably equidistantly spaced and serve as side inlet ports to permit the entry of blood through the side of cannula housing 12 and into exit section 20. Exit section 20 also includes a pump stator housing 42 possessing central hub 44 and pump stator blades 46 integrally connected to the central hub 44 and the outer wall of the exit section as shown in FIG. 6. Central hub 44 possesses stationary bearing pin 48 (FIG. 2) which is fixedly secured to the central hub 44 and serves to rotatably support the distal end of rotatable member 14. Exit section 20 also defines an axial opening or outlet port 50 to permit the pumped blood which entered through side ports 40 as well through openings 30 to exit cannula housing 12.

Flexible cannula 11 is preferably in the form of a tube placed over device 10 at the distal end to carry the pumped blood further in the artery. The cannula 11 preferably has a soft tip to avoid damage to the valve during insertion of the pump. The cannula optionally terminates in a solid hub and a plurality of spaced apart spokes similar to inlet section 16. It is preferably frictionally fit over device 10 although other modes of attachment are also contemplated.

Referring now to FIGS. 2–3, the motor unit of cannula pump 10 will be described. Rotating member 14 is supported for rotational movement within cannula housing 12 at one end by rotatable journal bearing 52 which is mounted about stationary bearing pin 28 and at the other end by rotatable journal bearing 54 which is mounted about stationary bearing pin 48. Journal bearings 52, 54 are fixedly secured within respective recesses 56, 58 formed in rotating member 14 and, thus, rotate with rotating member 14 about their respective stationary bearing pins 26, 48. Journal bearings 52, 54 are intended to absorb the thrust loads exerted by the action of rotating member 14 against the blood and are fabricated from a suitable material for this purpose such as ceramic or pyrolitic carbon.

Rotating member 14 has two sections, namely, rotor section 64 and impeller section 66. Rotor section 64 and impeller section 66 may be two separate components bonded to each other along adjacent end surfaces, as shown in the FIGS., or, in the alternative, may be a single component. Rotor section 64 has a built-in high energy bar or motor magnet 68 which cooperates with the magnetic fields produced by electromagnetic windings 36 to effectuate rotational movement of rotating member 14. The preferred materials of fabrication for rotor magnet 68 includes samarium-cobalt, neodymium-iron-boron, or any other suitable magnetizable material.

Referring still to FIGS. 2–3, rotating member 14 has a first or proximal set of blades 70 on rotor section 64 and a second or distal set of blades 72 on impeller section 66. In one embodiment shown in FIGS. 2, 3, and 7, each set of blades 70, 72 includes two diametrically opposed blades which provide for an axial flow type pumping action on the blood. In FIG. 7, only the impeller section 66 of rotating member 14 is shown since the blades 70 on rotor section 64 are identical. The blades 70, 72 preferably wrap about the perimeter of rotating member 14 for a distance between about ¼–¾ of the circumference of rotating member 14. Other blade arrangements are possible as well, particularly that of only a single blade configuration placed either at the rotor section 64 or impeller section 66. In particular, depending on the pumping parameters desired, the blade structure could be modified to provide a mixed flow (i.e., a blood flow having both an axial component and a centrifugal component). In addition, the number of blades in first and second sets of blades 70, 72 could be increased to three, for example, as shown in FIG. 8 or reduced to one single blade as shown in FIG. 9 to regulate the flow rate and back pressure of blood pumped by the cardiac support device. The direction of rotation and direction of blood flow is indicated by the arrows in FIGS. 7–9. Although shown as identical, it is also contemplated that the blade design for the rotor section 64 and the impeller section 66 could be different. The flow rate, typically referenced in liters/minute, is measured by the product of the velocity and cross-sectional area divided by the time. The velocity is measured as: meters/second.

In operation, the proximal set of blades 70 impart a pumping action to the blood entering into cannula housing 12 through axial inlet ports 30 and passing through the annular motor gap, referred to as the air gap, defined between rotor section 64 and inner tube 34 of cannula housing 12. The distal set of blades 72 impart mechanical energy to the blood entering cannula housing 12 through side inlet ports 40 and blood exiting the motor air gap and pumped by proximal blades 70. Thus, blood entering cannula housing 14 through axial inlet ports 30 initially passes over the proximal set of blades 70 within the motor chamber and then over the distal set of blades 72 within the pump chamber. Blood entering side inlet ports 42 passes over only the distal set of blades 72.

In a preferred embodiment, the volume of blood flow entering axial inlet ports 30 and passing through the motor air gap constitutes approximately ¼–⅓ of the total volume pumped (e.g., approximately 1–2 liters/min. out of total pump flow of 4–6 liters/min.) by device 10. The remaining blood flow enters side inlet ports 40 of cannula housing 12 to be directed over and acted upon by blades 72. Clearly other volume ratios of blood entry through the axial and side ports are contemplated.

Although the volume of blood flowing through the motor chamber in the preferred embodiment accounts for only ¼–⅓ of the total volume pumped by cardiac support device 10, this is a relatively significant amount of blood to pass through the motor air gap. The capability to accommodate a relatively large volume of blood through the motor air gap is attributed to the use of an ironless core copper electromagnetic windings 36 as opposed to employing copper windings supported by an iron core. The motor is a brushless motor to avoid mechanical failure of the brushes, e.g. arcing or wearing out, and to enable performance feedback, for better controlling the operation of the motor. Thus, the ironless core copper electromagnetic windings 36 occupy a significantly smaller cross-sectional area in the motor unit then a conventional iron core electromagnet winding, thereby increasing the total cross-sectional area of the motor air gap, i.e., the area defined between rotor section 64 and inner tube 34 of housing 12. As a result of this enlarged area of the air gap as provided through the incorporation of an ironless core copper electromagnetic windings 36, the following benefits are realized: 1) the motor unit can accommodate a greater volume of blood flow; 2) damage to the blood flowing through the motor is minimized since shearing of the blood with surfaces of the support device 10 is reduced; 3) a larger diameter rotor or rotor section 64 can be utilized which results in an increased cross-sectional area and an increase in blood flow; 4) sealing concerns of the motor and the moving components is essentially eliminated due to the aforementioned increase in the rate of blood flow through the device 10 and the motor air gap, which prevents blood from clotting within the motor without the need for dilution of the blood with saline or other fluids; 5) the blood constantly flows past the motor thereby eliminating any stagnation points which could result in blood clotting; and 6) the constant blood flow dissipates heat generated by the motor which could otherwise damage the blood.

Figure 10A:
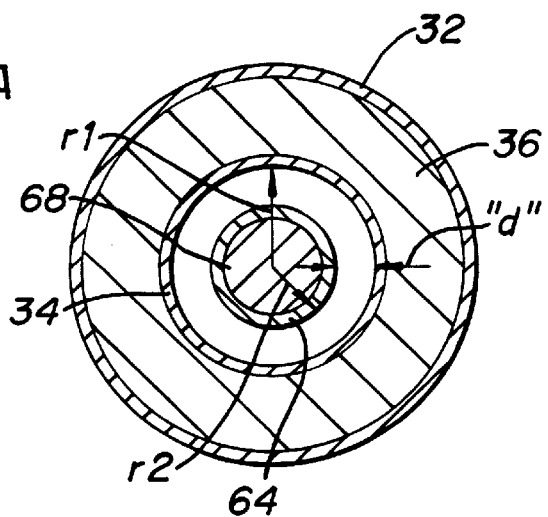
FIG. 10A is an axial cross-sectional view of the motor unit of the cardiac support device with the impeller blades removed to illustrate the cross-sectional area of the motor air gap provided with a motor unit having an iron core.
Figure 10B:
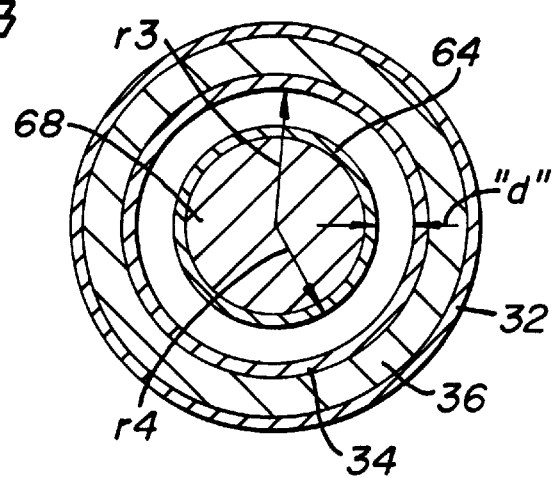
FIG. 10B is a view similar to the view of FIG. 10A illustrating the relatively enlarged cross-sectional area of the motor air gap as provided through the incorporation of an ironless core motor unit.

FIG. 10A is an axial cross-sectional view of the motor unit of the support device 10 with the first set of blades 70 of the motor section removed for illustrative purposes. In FIG. 10A, the motor unit is shown incorporating an iron core with conventional electromagnetic windings 36. FIG. 10B is a view similar to the view of FIG. 10A and illustrates the motor unit incorporating ironless core copper electromagnetic windings 36 in accordance with the preferred embodiment of the present disclosure. In both FIGS. 10A and 10B, the electromagnetic forces produced by the respective windings are comparable and the distance between rotor section 64 and inner tube 34, i.e., the distance "d" of the motor air gap, is identical. However, as can be seen by comparing FIGS. 10A and 10B, the ironless core copper windings 36 of the embodiment of FIG. 10B occupy a significantly smaller cross-sectional area than that occupied by the conventional windings of FIG. 10A.

Thus, as can be seen, the motor unit incorporating ironless core copper windings defines a motor air gap (space) with a greater total cross-sectional area to thereby accommodate a greater volume of blood and improve the pumping capabilities of the support device. As also depicted in the drawings, since the ironless core copper electromagnetic windings 36 (FIG. 10B) occupy a smaller area, a larger diameter rotor section or rotor 64 can be employed while maintaining the same distance "d" of the motor air gap, thus, further increasing the pumping capabilities of the device 10.

By way of example, a working embodiment of the motor unit of FIG. 10A has a rotor section 64 with a diameter of 0.165 inches and a motor air gap distance "d" of 0.025 inches. That is, the area A1 of the air gap in FIG. 10A is defined by;

$A1 = \pi r1^2 - \pi r2^2$, where r1 is the distance from the center of the motor to the inner wall of the inner tube 34; and r2 is the distance from the center of the motor to the outer wall of the rotor magnet 68.

By way of example, in a working embodiment of the motor unit of FIG. 10B incorporating copper windings 36, the diameter of rotor section 64 is 0.230 inches and the distance "d" of the motor air gap is identical to that of the motor unit of FIG. 10A, i.e., 0.025 inches.

The area A2 of the air gap in FIG. 10B is defined by;

$A2 = \pi r3^2 - \pi r4^2$, where r3 is the distance from the center of the motor to the inner wall of the inner tube 34; and r4 is the distance from the center of the motor to the outer wall of the rotor magnet 68.

To show by way of example the increased cross-sectional area of air gap FIG. 10B utilizing e.g. ironless core copper windings compared to FIG. 10A utilizing windings with an iron core; if r1=0.145 inches and r2=0.115 inches, the air gap area A1 would be 0.030 inches and the cross-sectional area of the air gap would be 0.0175 in$^2$. If, for comparative purposes, r3=0.108 inches, and r4=0.078 inches, the air gap A2 would be 0.030 inches and the cross-sectional area would be 0.025 in$^2$. Thus by keeping the overall diameter of the motor unit constant, e.g. at 0.402 inches, cross-sectional area of the air gap is increased by approximately 40%.

Figure 10C:
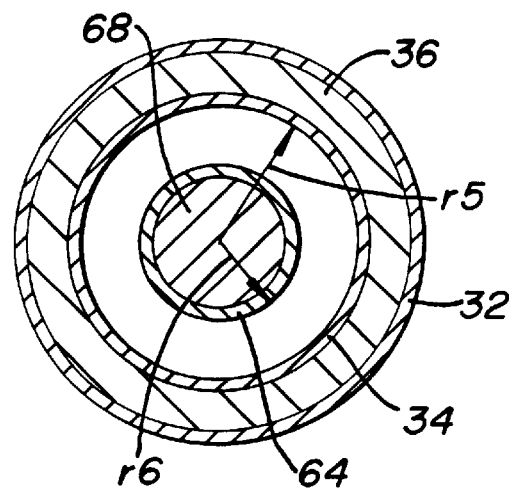
FIG. 10C is a view similar to the view of FIG. 10B illustrating an alternate embodiment of the ironless core motor unit where the diameter of the rotor is reduced to further increase the cross-sectional area of the motor air gap.

FIG. 10C depicts an alternate configuration of the motor unit of FIG. 10B. In this embodiment, the diameter of rotor section 64 is reduced to even further increase the cross-sectional area of the air gap between the motor stator (the motor stator being the portion of the pump including the electromagnetic windings 36) and rotor section 64. Although in this embodiment the magnetic field as generated by ironless core copper electromagnetic windings 36 is further from rotor magnet 68 of rotor section 64, the magnetic flux losses would be compensated by the longer moment arm as provided by the relatively long diameter of the rotor section 64 as compared to the diameter of the rotor for the stainless steel or iron core stator of FIG. 10A. Thus, the motor unit of FIG. 10C can accommodate an even larger volume of blood. By way of example, a working embodiment of the motor unit of FIG. 10C utilizes a rotor having a radius of 0.105 inches and provides a distance "d" of the motor air gap of 0.040 inches. The total cross-sectional area of the motor air gap is approximately 0.031 inches ($\pi r5^2 - \pi r6^2$). This represents an increase in cross-sectional area of approximately 80% over that of the iron core motor stator of FIG. 10A.

Referring now to FIG. 11, a generally schematic view of the heart showing two devices 10 of the present disclosure inserted for support of both the left heart function and the right heart function is illustrated. It should be understood that in the alternative, only one support device can be used to support either the left or the right heart function. In the illustrated embodiment, the left ventricle, generally indicated at A, contains one device 10 and the right ventricle, indicated at B, contains another device 10. The outflow portions of the support devices 10 deliver blood respectively from the left ventricle A into the aorta C, and from the right ventricle B into the pulmonary artery D. As previously described, the blood enters through axial ports 30 and side ports 40 as indicated by the directional arrows 25, 27 and is emitted through the outflow opening 50 as shown. Thus, the support devices 10 intake blood from both ventricles A, B and pump the blood into the two main arteries C, D. Since the entire volume of blood within the support device 10 remains within the ventricles or arteries, it is appropriate to consider that the priming blood volume of this pump is essentially zero. That is, no blood need be withdrawn from the cardiovascular system to fill the pump and tubing circuit with this embodiment.

Each device 10 is respectively inserted through a small incision in the apex of either ventricle and may be held there by a purse-string suture (not shown). Since in this embodiment the devices 10 are inserted when the patient's open chest is open and the heart is exposed, the surgeon can readily feel the heart and easily ascertain that the tip of the flexible cannula 11 has passed across the proper valve, i.e., the aortic valve or pulmonary artery valve, and into the aorta or pulmonary artery as desired, rather than across an inflow valve and into the left atrium or right atrium, which would be improper. The anatomy of the heart makes proper placement relatively simple and direct path from the apex to the aorta and to the pulmonary artery. With support devices 10 inserted in the fashion shown in FIG. 11, the outflow valve, that is the aortic valve or pulmonary valve, is able to close around the outside of the flexible cannula 11 thereby permitting a sufficient seal to prevent major leakage back from the artery into the respective ventricle A,B. Thus, support devices 10 may be applied and sealed by the aortic or pulmonary valves thereby leaving the valves undamaged.

It is also to be appreciated that in the alternative, the entire support device 10 can be positioned within the heart.

Referring now to FIGS. 12–13, there is illustrated an alternate method for positioning support device 10 within the patient's heart. In accordance with this method, support device 10 is inserted utilizing endoscopic (thoracocospic) surgical techniques. In endoscopic procedures, surgery is performed in the body through narrow endoscopic tubes or portals inserted through small entrance wounds in the skin. Endoscopic procedures, by being less invasive, have the advantage of reducing the patient's recovery time and thereby reducing costs.

In accordance with the endoscopic method, an endoscopic tube or portal 80 is positioned within the patient's chest cavity to access the heart area as shown. The endoscopic tube 80 may be positioned proximal to the abdominal cavity Any within adjacent ribs to access the open area of the heart. In this application, the endoscopic portal 80 would be in an offset position as shown in FIG. 12 to avoid the sternum bone. Typically, at least a second endoscopic portal 82 would be positioned within the chest cavity to permit the insertion of an endoscope to view the procedure being performed. It is also envisioned that additional endoscopic portals may be utilized to permit the introduction of endoscopic surgical instrumentation into the chest cavity to assist the surgeon in accessing the heart and positioning the support device 10 within the heart. Further, another endoscopic tube 84 would be utilized if two support devices 10, one for each side of the heart, are to be used. A cuff 86 may also be utilized to restrict blood flow when the support device 10 is inserted. Cuff 86 has a flexible tube portion 87 configured to receive the support device 10 and a flange 88 which is attached to the apex by glue, staples or other fastening means. The endoscopic portal 80 is inserted through cuff 86 to provide an access port for the support device 10. The support device 10 is inserted through the port 80 and cuff 86. A similar cuff can be utilized in conjunction with endoscopic portal 84 if a second support device 10 is utilized.

With the endoscopic portals and instrumentation appropriately placed, the support device 10 is inserted through endoscopic portal 80 to a position adjacent the apex of the heart as shown in FIG. 13. The heart is accessed by, e.g., making an incision in the heart wall by an appropriate incising instrument inserted through an endoscopic tube, and the support device 10 is placed within the ventricle of the heart. The support device 10 is preferably positioned within the heart as illustrated in FIG. 11 whereby the outlet port 50 of the support device 10 is adjacent the corresponding artery. The support device 10 may be secured in place with the use of purse string stitches or the like as mentioned above. If two pumps are to be inserted, one in each ventricle, an access port for each device 10 would be required.

FIG. 14 illustrates another endoscopic method for applying the cardiac support device 10. In accordance with this method, an endoscopic portal 80 is positioned to access the aorta C. Preferably, the portal 80 is positioned under the clavicle between the first and second ribs. Thereafter, the device 10 is inserted within the portal 80 and advanced to the aorta C. A cuff such as that described above could be utilized and attached to the aorta to contain the blood. The support device 10 is inserted within the aorta through, for example, an incision formed in the outer wall of the aorta by an incising instrument inserted through an endoscopic port and maneuvered down into the left ventricle through the aorta C to any of the positions shown in FIG. 11. The device 10 is oriented within portal 80 such that the rear end of the device 10, i.e., the end having the motor unit, exits the portal 80 first and is dropped down into the left ventricle. In this manner, the outlet port 50 is adjacent the aorta C as shown in FIG. 11. It could alternatively be inserted into the left subclavian artery. It is also envisioned that the pulmonary artery could be accessed and the device 10 maneuvered into the right ventricle B in a similar manner.

Referring now to FIG. 15, alternate embodiment of the cardiac support device of the present disclosure is illustrated. Cardiac support device 100 includes cannula housing 102 having motor section 104 and pump section 106. Motor section 104 defines a tapered portion 108 of reduced cross-section at one end which is connected to the impeller section 106 by support pins 110. Support pins 110 are preferably embedded within each section 104, 106 to fixedly connect the two components. A plurality of inlet ports 112 are defined about tapered portion 108 of motor section 104 between adjacent support pins 110 to permit the direct entry of blood within impeller section 106 of cannula housing 102. Inlet ports 112 are generally axially disposed openings and, thus, provide an axial path for blood to enter cannula housing 102 at this intermediate location. Pump section 106 possesses pump stator housing 114 having central hub 116 and pump stator blades 118.

Rotating member 120 of device 10 includes rotor section 122 and impeller section 124 connected to the rotor section 122 by rotating drive shaft 126. Drive shaft 126 is securely connected to each section 122, 124 thus providing for corresponding rotational movement of the two components. Rotor section 122 includes rotor magnet 128 (as shown in phantom) and rotor blade 130 (also shown in phantom). Impeller section 124 includes impeller blade 132. Rotating member 120 is supported for rotational movement in a manner similar to that described in connection with the embodiment of FIG. 1.

An elongated cannula portion 134 is connected to pump section 104 of device 100 and extends beyond pump stator housing 114. Elongated cannula portion 134 is typically at least partially positioned within a respective artery associated with either the left or right ventricles to ensure the outlet opening of cannula housing 102 is disposed within the artery.

As previously described, rotor section 122 and impeller section 124 each includes only one blade member, i.e., rotor blade 130 and impeller blade 132. As best shown in the cross-sectional view of FIG. 16, rotor blade 130 extends about rotating member 120 for a distance of about ⅓ or less of the circumference of the rotating member 120. Impeller blade 132 extends about rotating member 120 for a distance of about ⅔ or more of the circumference of the rotating member 120. Rotor blade 130 can possess this relatively small dimension since the volume of blood pumped by this blade 130 is small compared to the total volume pumped by device 10 (i.e., 1–2 liters/min. of 4–6 liters/min.). The two blades 130, 132 are preferably disposed substantially opposite each other or diametrically opposed on their respective sections 122, 124 of rotating member 114 so as to minimize the radial imbalance of the rotating member 114. Other blade configuration are envisioned as well including the blade configurations of FIGS. 7–9.

Blood entering cannula housing 102 through axial inlet ports 30 defined between adjacent spokes 26 of cannula housing 102 passes through the motor air gap defined between inner tube 34 and rotor section 122 of rotating member 114 where the blood is acted upon by single rotor blade 130. The blood is then directed through the interior of tapered portion 108 within an annular space defined between rotating drive shaft 126 and the inner wall of the tapered portion 108 and released through an exit opening of the tapered portion into pump section 106 of cannula housing 102. Impeller blade 126 imparts mechanical energy to the blood and directs the blood over stator blades 126 through the longitudinal opening of cannula portion 134.

Blood entering directly through inlet ports 112 is acted upon by impeller blade 132 of impeller section 124 and pumped through cannula portion 134. Since inlet ports 112 are generally axial openings, the blood entering the ports 112 takes a direct axial path into cannula housing 102 coincident with the path the blood takes through pump section 106 across impeller blade 132, thus, enhancing the pumping capabilities of support device 100. This device 100 can be inserted into the heart in similar ways as the device 10 discussed above.

The support devices of FIGS. 1 and 15 can be fabricated utilizing primarily injection-molded, polymeric materials permitting low cost and disposability of the cannula housings and pumps themselves. The electric motors may be provided in a reusable configuration or may be made very inexpensive to make it economically feasible to dispose of the motors after use.

While the above description contains many specifics, these specifics should not be construed as limitations, on the scope, but merely as an exemplification of a preferred embodiment thereof. For example, the blade arrangement of the embodiment of FIG. 15 can be incorporated in the embodiment of FIG. 1. Those skilled in the art will envision other possible variations that are within the scope and spirit of the claims appended hereto.

What is claimed is:

1. An apparatus for pumping blood, which comprises:
   a) an elongated housing adapted to be at least partially positioned within the heart of a patient, the elongated housing including an outer wall having first and second ends and defining a longitudinal axis, the elongated housing having at least a first inlet port for permitting blood to enter the elongated housing through the first end of the elongated housing and at least a second inlet port defined in the outer wall of the elongated housing and being axially displaced from the first inlet port for permitting blood to enter through the outer wall, the second end of the elongated housing being open to define an axial outlet opening to permit the blood to exit the elongated housing;
   b) a rotating member supported for rotational movement within the elongated housing and rotatable to impart pumping energy to the blood entering through the first and second inlet ports to direct the blood through the outlet opening of the elongated housing; and
   c) a motor unit contained within the elongated housing for imparting rotational movement to the rotating member.

2. The apparatus according to claim 1 wherein the first end of the elongated housing defines an axial opening such that the first inlet port is an axial inlet port.

3. The apparatus according to claim 1 including a plurality of second inlet ports defined in the outer wall of the elongated housing.

4. The apparatus according to claim 1 wherein the rotating member includes first and second blood pumping blade arrangements, the first blade arrangement dimensioned to impart pump energy to the blood entering the elongated housing through the first inlet port, the second blade arrangement dimensioned to at least impart pump energy to the blood entering the elongated housing through the second inlet port.

5. The apparatus according to claim 4 wherein the first and second blade arrangements each include at least one blade mounted to the rotatable member.

6. The apparatus according to claim 5 wherein the rotating member defines a periphery having a predetermined distance and wherein the first blade arrangement includes a first blade which extends about ⅓ of the predetermined distance of the rotating member and wherein the second blade arrangement includes a second blade which extends about ⅔ of the predetermined distance of the rotating member, the positions of the first and second blades being substantially opposite one another so as to minimize radial imbalance of the rotating member.

7. The apparatus according to claim 1 wherein the motor unit includes an electric motor, the electric motor including a magnetically actuated rotor and a motor stator.

8. The apparatus according to claim 7 wherein the rotor of the electric motor is embedded within the rotatable member.

9. The apparatus according to claim 1 wherein the first and second inlet ports are axially displaced relative to each other.

10. An apparatus for pumping blood, which comprises:

a) an elongated housing dimensioned to be at least partially positioned within the heart of a patient, the elongated housing including an outer wall, at least a first inlet port for permitting blood to enter the elongated housing through a first end of the elongated housing and at least a second inlet port defined in the outer wall of the elongated housing for permitting blood to enter through the outer wall;

b) a rotating member supported for rotational movement within the elongated housing and rotatable to impart pumping energy to the blood entering through the first and second inlet ports to direct the blood through an outlet opening of the elongated housing; and c) an electric motor for imparting rotational movement to the rotating member, the electric motor including a magnetically actuated rotor embedded within the rotatable member and a motor stator, the rotatable member and the motor stator defining an annular space therebetween through which blood entering the first inlet passes.

11. An apparatus for pumping blood, which comprises:

a) an elongated housing dimensioned to be at least partially positioned within the heart of a patient, the elongated housing including an outer wall, at least a first inlet port for permitting blood to enter the elongated housing through a first end of the elongated housing and at least a second inlet port defined in the outer wall of the elongated housing for permitting blood to enter through the outer wall;

b) a rotating member supported for rotational movement within the elongated housing and rotatable to impart pumping energy to the blood entering through the first and second inlet ports to direct the blood through an outlet opening of the elongated housing; and c) an electric motor for imparting rotational movement to the rotating member, the electric motor including a magnetically actuated rotor and a motor stator, the motor stator including ironless core copper electromagnetic windings.

12. An apparatus for pumping blood, which comprises:

a) an elongated housing defining a generally longitudinal axis and having at least one opening at a first axial location to permit blood to enter the elongated housing at the first axial location and at least one opening at a second axial location axially displaced from the first axial location to permit blood to enter the elongated housing at the second axial location, and further having an exit opening to permit blood to exit the elongated housing;

b) a rotating member adapted for rotational movement within the elongated housing, the rotating member including first and second blood pumping blade arrangements, the first blade arrangement for imparting pump energy to the blood entering the elongated housing through the opening at the first axial location, the second blade arrangement axially displaced from the first blade arrangement for imparting pump energy to the blood entering the elongated housing through the one opening at the second axial location; and c) a drive mechanism disposed within the elongated housing for imparting rotational movement to the rotating member.

13. The apparatus according to claim 12 wherein the one opening at the first axial location is an open end of the elongated housing.

14. The apparatus according to claim 12, wherein the first and second blade arrangements are substantially identical in configuration.

15. An apparatus for pumping blood, which comprises:

an elongated housing member including a motor chamber and a pump chamber, the housing member having at least a first opening to permit blood to enter the motor chamber and at least a second opening to permit blood to enter the pump chamber, the housing member further including an outflow opening to permit blood to exit the housing member;

a rotatable member adapted for rotational movement within the housing to impart pumping energy to blood entering the motor and pump chambers through respective first and second openings of the housing member; and an electric motor disposed within the motor chamber for imparting rotational movement to the rotatable member, the electric motor including a magnetically actuated rotor mounted to the rotatable member and a motor stator, the rotatable member and the motor stator defining a space therebetween through which blood entering the first opening passes through the motor chamber.

16. The apparatus according to claim 15 wherein the rotatable member traverses at least portion of the motor chamber and the pump chamber.

17. The apparatus according to claim 16, wherein the motor unit includes an ironless core motor with copper windings.

18. The apparatus according to claim 17, wherein the cross-sectional area of the space between the rotatable member and the motor stator ranges from approximately 0.025 in$^2$ to approximately 0.031 in$^2$.

19. The apparatus according to claim 16 wherein the rotatable member includes a first blade arrangement for imparting pump energy to blood entering the first opening and passing through the motor chamber within the space defined between the rotatable member and the motor stator and a second blade arrangement for imparting pump energy to blood both entering the second opening and exiting the motor chamber.

20. The apparatus according to claim 15 wherein the first and second openings in the elongated housing member are generally axial openings.

21. The apparatus according to claim 15 including a cannula portion connected to the housing member adjacent the outflow opening, the cannula portion dimensioned to be placed in an artery associated with a patient's heart and defining a longitudinal opening therethrough to permit blood to pass.

22. A cardiac support device, which comprises:

an elongated housing member having axial inflow and axial outflow openings defined in respective first and second ends of the elongated housing, the elongated housing further including a radial inflow opening in an outer wall of the housing member;

an impeller mounted for rotational movement to impart mechanical energy to blood entering the axial inflow opening and the radial inflow opening to direct the blood through the outflow opening; and an electric motor disposed within the elongated housing, the electric motor including a motor stator and a rotor rotatable within the motor stator to impart rotational movement to the impeller, the motor stator and the rotor defining a space therebetween through which blood entering the axial inflow opening passes to be expelled from the axial outflow opening.

23. A cardiac support device which comprises:

an elongated housing member having axial inflow and axial outflow openings defined in respective first and second ends of the elongated housing;

an impeller mounted for rotational movement to impact mechanical energy to blood entering the axial inflow opening to direct the blood through the outflow opening; and an electric motor disposed within the elongated housing, the electric motor including a motor stator having ironless core copper windings and a rotor rotatable within the motor stator to impart rotational movement to the impeller, the motor stator and rotor defining a space therebetween through which blood entering the axial inflow opening passes to be expelled from the outflow axial opening.

24. The device according to claim 23, wherein the cross-sectional area of the space between the rotatable member and the motor stator ranges from approximately 0.025 in to approximately 0.031 in.

* * * * *